US006821246B2

(12) United States Patent
Kasel et al.

(10) Patent No.: US 6,821,246 B2
(45) Date of Patent: Nov. 23, 2004

(54) ENDOSCOPE FITTED WITH A WINDOW COVERING A LIGHT GUIDE AND AN IMAGE TRANSMITTER

(75) Inventors: Manfred Kasel, Norderstedt (DE); Thomas Reher, Hittbergen (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 66 days.

(21) Appl. No.: 10/323,317

(22) Filed: Dec. 18, 2002

(65) Prior Publication Data

US 2003/0153813 A1 Aug. 14, 2003

(30) Foreign Application Priority Data

Feb. 12, 2002 (DE) ......................................... 102 05 735

(51) Int. Cl.⁷ ................................................. A61B 1/06
(52) U.S. Cl. ........................ 600/176; 600/129; 600/177
(58) Field of Search ............................... 600/109, 160, 600/169, 170, 173, 175, 176, 177, 127, 129

(56) References Cited

U.S. PATENT DOCUMENTS

| 4,419,987 A | * | 12/1983 | Ogiu | ............................. | 128/4 |
| 5,377,669 A | * | 1/1995 | Schulz | ............................ | 128/6 |
| 5,603,687 A | * | 2/1997 | Hori et al. | ................... | 600/166 |
| 5,980,453 A | * | 11/1999 | Forkey et al. | ............... | 600/162 |
| 6,503,196 B1 | * | 1/2003 | Kehr et al. | .................. | 600/176 |
| 6,537,209 B1 | * | 3/2003 | Pinkhasik et al. | ........... | 600/170 |
| 2001/0023314 A1 | * | 9/2001 | Bodol et al. | ................ | 600/172 |

FOREIGN PATENT DOCUMENTS

DE        195 25 995 C1        7/1995

* cited by examiner

Primary Examiner—Beverly M. Flanagan
(74) Attorney, Agent, or Firm—Rankin, Hill, Porter & Clark LLP

(57) ABSTRACT

A rigid endoscope optics including an outer tube (1) of which the distal aperture is closed by a window (2) affixed to the outer tube in a sealed manner. The outer tube encloses an image transmitter (4, 5) running through it and a light guide (6) running parallel to the transmitter, the transmitter and pipe being configured by their distal ends (5, 7) looking and radiating, respectively, through the window. The light guide is cross-sectionally separated from the image transmitter's cross-section at least in the region of defined between their distal ends and the window by an optically opaque partition (3). The partition rests by its distal edge against the window, wherein an elastic and opague insert is disposed between the distal end of the partition (3) against the window (2).

3 Claims, 1 Drawing Sheet

ENDOSCOPE FITTED WITH A WINDOW COVERING A LIGHT GUIDE AND AN IMAGE TRANSMITTER

BACKGROUND OF THE INVENTION

1. Field of the Invention

The present invention relates to an endoscope optics having a sealed outer tube in which a window is directly affixed to a distal end of the outer tube.

2. Description of Related Art

Endoscope optics of the aforementioned type are known in the state of the art, as shown in the German patent document 195 25 995 C1. The endoscope optics of this kind offer the substantial advantage of the window being directly affixed in the outer tube of which it covers the full cross-section and being perfectly sealed off for instance by soldering. Accordingly, the entire space inside the outer tube, which contains contamination-susceptible optical components and optical surfaces, is hermetically sealed. Such a design reliably secures the optics against invading liquids and vapors, which is particularly troublesome under the critical conditions of steam autoclaving to sterilize endoscope optics for medical applications.

However, optics of this kind, namely fitted with a window jointly covering the cross-sectional zone of the light guide and the image transmitter, incur the problem that the light radiates from the exit of the light guide into the distal entry end of the image transmitter. Such light radiation creates interfering light reflections in the image. As already discussed in the above cited document, light entering the window is reflected by the window and may be directed toward the light transmitter. As a result, the aforementioned German patent document assumes that direct light penetration from the light guide into the image transmitter no longer can take place in front of the window because direct light penetration is precluded by a partition.

Now it has been found that such an assumption is unwarranted. To a substantially interfering degree, light also passes through a gap between the distal edge of the partition and the window. Accordingly, the construction of the state of the art continues to suffer from unwanted light pollution created by light passing between the from the light guide into the image transmitter.

SUMMARY OF THE INVENTION

The present invention is directed toward precluding light penetration otherwise taking place already in front of the window.

The present invention is based on the insight that the known design of the above cited kind, wherein a partition internally and directly abuts the window, is unable to prevent light penetration inside this window. The partition and the outer tube undergo different thermal expansions. It must be borne in mind in this respect that endoscope optics of the above kind are subjected to high temperature fluctuations. When typically used in medical applications, temperature changes in the first place arise between room and body temperatures. During conventional steam sterilization, the optics is raised from room temperature to above 120° C. and then is cooled to room temperature again. If the partition is designed to always abut the window in light-tight manner, then, in the presence of longitudinal thermal expansion, the partition will excessively stress the window and break it. If the partition's length is selected so that it does not pressurize the window during such longitudinal thermal expansion, then a gap will necessarily exist between the partition distal wall and the window. Such a gap may transmit light.

Accordingly the present invention provides that the distal edge of the partition rests, by means of an elastic, light-tight insert, against the window. The insert assures optical sealing of the gap under all conditions of partition expansion, and this without unduly stressing said window. Accordingly the design of the present invention reliably prevents light from entering the image transmitter within the window, and removes the risk or danger of the window breaking. Tests have shown that as a result of the sealing operation of the insert, the essential portion of the interfering light penetration is precluded. An optics of the invention is applicable without suffering from significant light reflections. The invention also applies to all design variations and in particular, to endoscope optics with optic fiber cables as light guides and to image transmitters both in the form of optic fiber bundles and in the form of systems of relay lens elements. The partition may be configured at arbitrary cross-sections between the two cross-sectional zones, in particular in conventional manner as a system tube enclosing the image transmitter. Advantageously, the partition shall run not only across the range between the distal ends of light guide and image transmitter and the window, but also over the essential length of the light guide in order to avert also light penetration in a rear zone.

The spacer illustratively may be in the form of an adhesive connection of a material that was deposited as a liquid. However, in further accordance with the present invention, the spacer is an elongated, preferably flexible, body in the form of a loop, and thereby offers manufacturing and cost advantages resulting from such being separately or previously manufacturable.

BRIEF DESCRIPTION OF THE DRAWINGS

These and further features of the present invention will be apparent with reference to the following description and drawings, wherein.

DETAILED DESCRIPTION OF THE PREFERRED EMBODIMENTS

Figure 1:
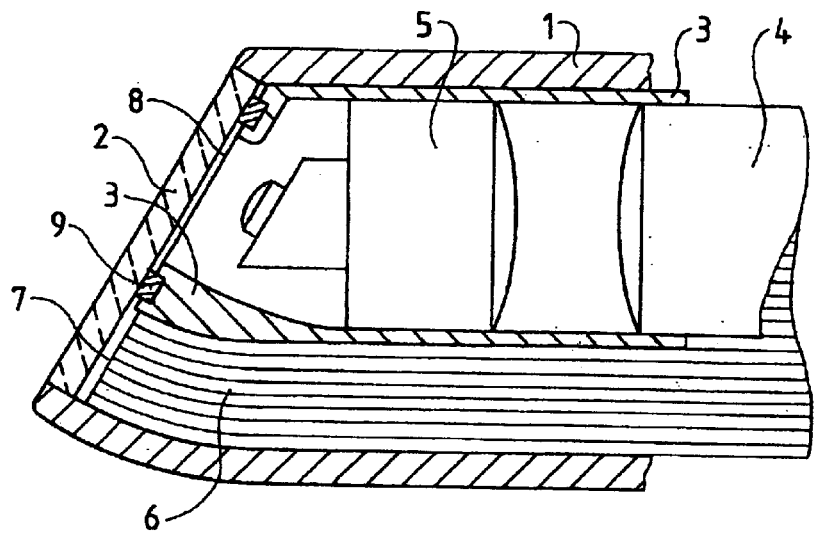
FIG. 1 is an axial section of the distal end zone of an endoscope optics according to the present invention.
Figure 2:
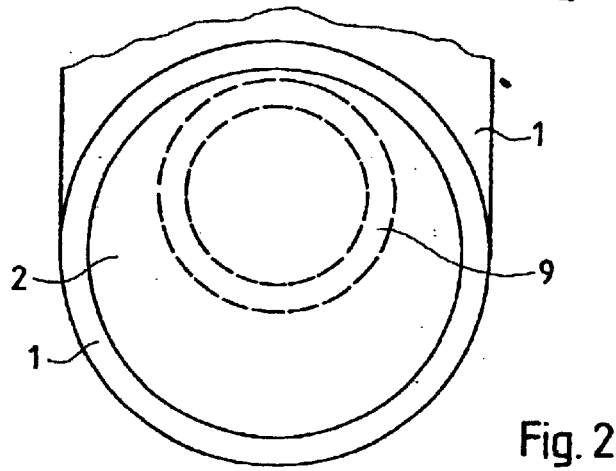
FIG. 2 is a front view perpendicularly to the window of the endoscope optics of FIG. 1; and, FIG. 3 is an elevation in the manner of FIG. 2 of an embodiment variation.

FIGS. 1 and 2 show the distal end zone of an endoscope according to the present invention. The endoscope has an outer tube 1, which is conventionally made of an appropriate metal. A window 2, which is made of an appropriate glass, is sealingly inserted in a distal end of the outer tube 1. The window 2 is sealed to the outer tube by conventional soldering along the edges of the window.

In the shown assembly, a system tube 3 rests inside the outer tube 1 and encloses an image transmitter in the form of the shown system of relay lens elements 4 and a distally mounted conventional objective lens 5. Again, the conventional system tube 3 is made of an appropriate metal.

The residual inside cross-section of the outer tube 1 assumes a substantially half-moon shape (FIG. 2) on the outside and is filled with a light guide in the form of an optic fiber bundle 6 terminating in a distal end face 7.

The opaque system tube 3 precludes light radiation within the outer tube 1 between the cross-sectional zone of the optic fiber bundle 6 and the cross-sectional zone of the image transmitter 4, 5. Accordingly the system tube 3 constitutes an opaque partition between the light guide 6 and the image transmitter 4, 5.

By its distal edge 8, the system tube 3 acting as the partition abuts the window 2, namely by means of an insert which in this embodiment assumes the shape of an O-ring 9 that, as shown in FIGS. 1 and 2, runs annularly along the distal edge of the system tube 3. As shown in FIG. 1, the O-ring 9 of this embodiment rests in a groove in the end face of the edge of the system tube 3. In this embodiment the system tube 3 is appropriately thicker in its distal end zone.

The insert or O-ring 9 is made of an elastic opaque material and rests at a given compression against the window 2 as shown by the annular surface 9 indicated by dashed lines. Illustratively the O-ring may be made of a black rubber.

When light exits the end face 7 of the optic fiber bundle 6, some of it will radiate laterally or will be reflected from the inside surface of the window 2, respectively. This light is incident on the gap between the system tube 3 and the window 2 and might pass through this gap to the objective lens 5 of the image transmitter. However, the O-ring 9 optically seals off this gap and precludes light penetration through the gap. The elastic O-ring 9 also assures that in the event of large thermal expansions of the system tube 3, the forces acting on the window 2 shall remain small enough that destruction by thermal stress of the window need not be feared.

Figure 3:
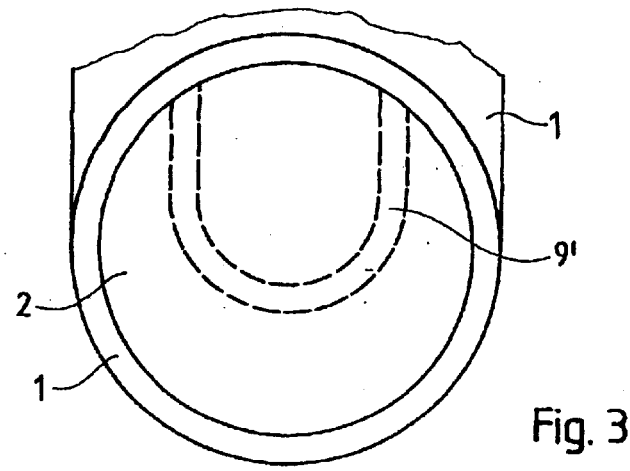

The shown optic-fiber bundle 6 also may be replaced by another light guide, for instance a hose-like liquid light guide, an acrylic bar or the like. Instead of the shown system of relay lens elements 4, 5, another image transmitter, for instance in the form of an optic fiber bundle, may be used. Such an optic fiber bundle may, for example, assume a non-circular cross section in which case the partition between image transmitter and light guide then may assume other shapes, such as the tubular form shown in FIGS. 1 and 2. For instance, the partition shape shown in FIG. 3 may the embodiment variant assuming the U-shaped geometry 9'. As regards the array of relay lens elements 4, 5 shown in FIG. 1, the geometry shown in FIG. 3 may be present in the distal end zone whereas the system tube 3 will be circular in the remaining region.

An insert other than the shown O-ring 9 also may be used between the distal edge of the system tube 3 or between another partition and the window 2. For instance the insert may be in the form of an adhesive layer that was deposited in liquid form. However, the material used for the insert must be as opaque and elastic as possible in order to rest in well-sealing manner against the window 2.

What is claimed is:

1. A rigid endoscope optics comprising an outer tube (1) of which the distal aperture is closed by a window (2), said window being sealingly secured at said distal aperture, said outer tube enclosing an image transmitter (4, 5) running through said outer tube and a light guide (6) running parallel to said image transmitter, said image transmitter and light guide being configured such that their distal ends (5, 7) look and radiate, respectively, through the window, a part of a cross-section of the outer tube accommodating the light guide is separated from a cross-section of the outer tube accommodating the image transmitter at least in a region disposed between their distal ends and the window, by an optically opaque partition (3), and wherein an elastic and opaque insert (9) is disposed between a distal edge of the partition (3) and the window (2).

2. The endoscope as claimed in claim 1, wherein the insert is shaped as a loop (9) to constitute an O-ring.

3. The endoscope as claimed in claim 2, wherein the loop (9) rests in a groove formed in an end face of the partition distal edge.

* * * * *